United States Patent [19]

Edwards

[11] Patent Number: 4,874,367
[45] Date of Patent: Oct. 17, 1989

[54] HYPODERMIC JET INJECTOR AND CARTRIDGE THEREFOR

[75] Inventor: Bryant Edwards, Clarendon Hills, Ill.

[73] Assignee: Marpam International, Inc., Clarendon Hills, Ill.

[21] Appl. No.: 152,467

[22] Filed: Feb. 5, 1988

[51] Int. Cl.⁴ ............................................. A61M 5/30
[52] U.S. Cl. ........................................ 604/72; 604/68
[58] Field of Search ................................... 604/68–72

[56] References Cited

U.S. PATENT DOCUMENTS

| | | | |
|---|---|---|---|
| 2,681,653 | 6/1954 | Kuhne | 604/68 |
| 2,704,542 | 3/1955 | Scherer | 604/68 |
| 2,816,543 | 12/1957 | Verditty et al. | 604/68 |
| 2,902,994 | 9/1959 | Scherer | 604/68 |
| 3,138,157 | 6/1964 | Ziherl et al. | 604/71 |
| 3,782,380 | 1/1974 | Van Der Gaust | 604/68 |
| 4,623,332 | 11/1986 | Lindmayer et al. | 604/68 |
| 4,680,027 | 7/1987 | Parsons et al. | 604/68 |
| 4,722,728 | 2/1988 | Dixon | 604/68 |

Primary Examiner—Max Hindenburg
Assistant Examiner—K. M. Reichle
Attorney, Agent, or Firm—Cook & Egan, Ltd.

[57] ABSTRACT

A hypodermic jet injector includes a resuable, spring-powered gun and a disposable unitary cartridge filled with a substance to be injected. The unitary cartridge has an interrupted flange which cooperates with a shoulder on the gun to releasably affix the cartridge to the end of the gun for use. A predetermined amount of sterile medicament is readily injected from the sterile end of the cartridge without the need to sterilize the gun. This is particularly useful for self-administration of drugs and medicines by the patient.

6 Claims, 1 Drawing Sheet

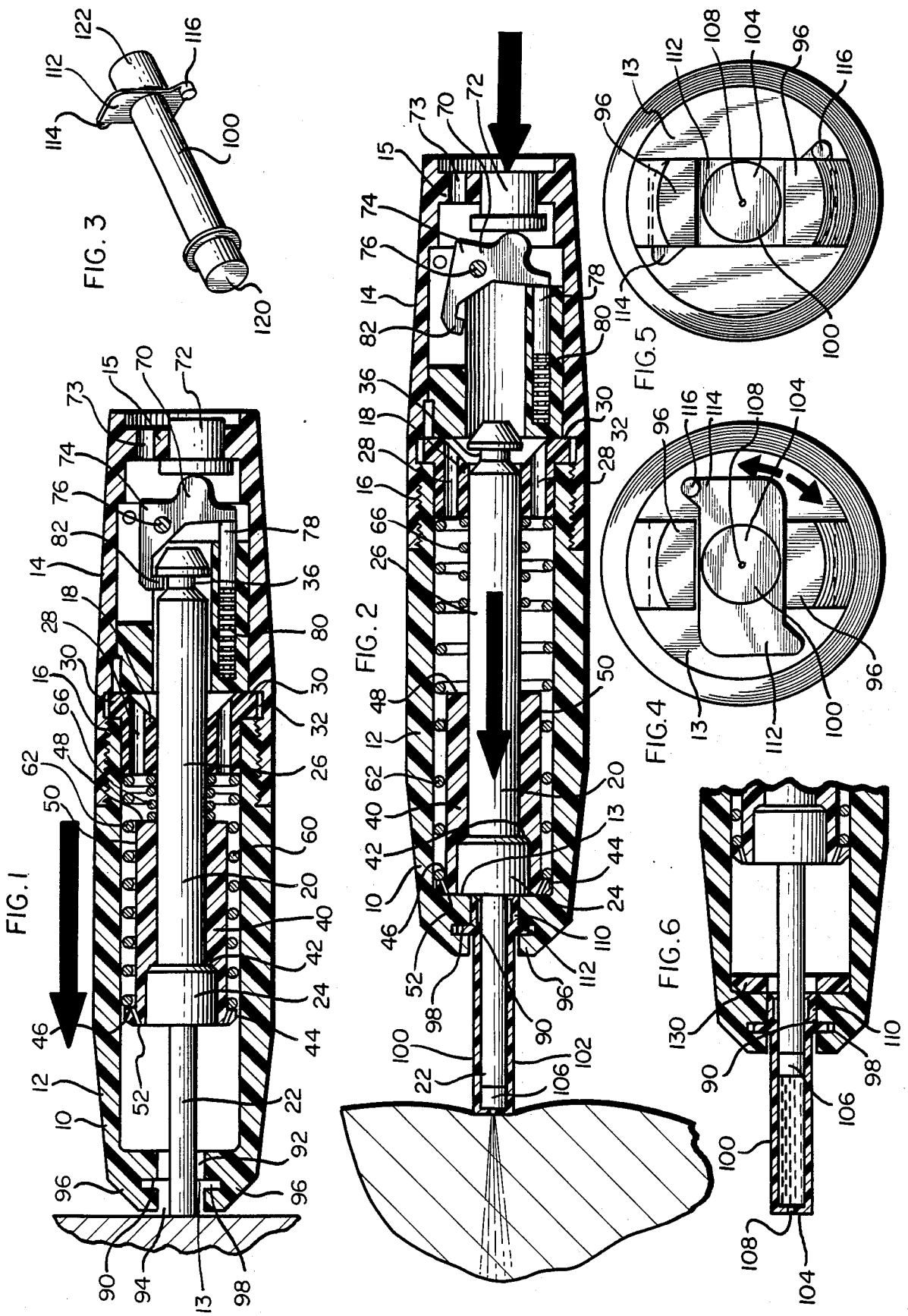

HYPODERMIC JET INJECTOR AND CARTRIDGE THEREFOR

The present invention relates to a needleless hypodermic jet injector device which includes a reusable, springpowered gun and a disposable cartridge filled with the substance (i.e., medicament) to be injected. More particularly, the present invention relates to a sterile, disposable cartridge containing a predetermined amount of medicament, which may be readily locked onto the gun for use. The spring powered gun, which need not be sterile, may be readily fired to inject the medicament from the sterile, disposable cartridge through the skin into the subject. The hypodermic jet injector of the present invention is particularly useful for self-administration of drugs and medicines by the patient.

THE PRIOR ART

It has been recognized that medication and other substances may be injected beneath the skin of humans or animals, without the use of a needle, through the use of high a pressure jet. Hypodermic jet injectors capable of needleless injection have achieved patient acceptance because a needle is not required and because the injection causes little or no pain.

The jet injector devices which have been marketed heretofor have been large, expensive units, generally adapted to retain large quantities of medicament for repeated injections. Most of these machines are not portable and are used chiefly for mass innoculation programs. Such machines are not adapted to self-administration use by the patient. Such cumbersome and expensive units have meant that the use of high pressure jet-injecting devices have been limited. Patents which describe multi-dose jet injectors include U.S. Pat. No. 2,785,678 to Hein; U.S. Pat. No. 3,330,276 to Gordon; U.S. Pat. No. 3,521,633 to Yahner; U.S. Pat. No. 3,908,651 to Fudge; U.S. Pat. No. 4,059,107 to Iriguchi et al.; U.S. Pat. No 4,447,225 to Taff et al.; and U.S. Pat. No. 4,560,377 to Geat et al.

The prior art has also developed some relatively small jet injector devices which are powered by compressed gas. Again, these devices have been generally expensive and somewhat difficult to use. Further, as the gas supply is consumed, the gas driving force changes. Moreover, the gas is subjected to pressure fluctuations caused by changes in the ambient atmosphere temperature. Patents which describe such gas powered injectors include U.S. Pat. No. 3,115,133 to Morando; U.S. Pat. No. 3,527,212 to Clark; U.S. Pat. No. 3,688,765 to Gasaway; U.S. Pat. No. 3,853,125 to Clark et al.; and U.S. Pat. No. 3,945,379 to Pritz et al. The gas powered devices have not achieved significant commercial success.

Further, the prior art discloses a number of spring powered jet injectors. While these prior art devices overcome some of the problems encountered with the multi-dose injectors and the gas powered injectors, the prior art spring powered injectors rely on complex filling techniques or large difficult to use cartridges from which the medicament is dispensed. Examples of the spring powered injectors are U.S. Pat. No. 2,380,534 to Lockhart; U.S. Pat. No. 2,722,931 to May; U.S. Pat. No. 2,762,370 to Venditty; U.S. Pat. No. 3,131,692 to Love; U.S. Pat. No. 3,557,784 to Shields; and U.S. Pat. No. 3,782,380 to Van Der Gaast. The devices described in these patents have not achieved significant commercial success.

Some of the foregoing patents describe jet injectors in which the medicament to be dispensed is first drawn into the injector and then dispensed. A wide variety of techniques for filling the injectors and injecting the medicament therefrom have been suggested. Some of these prior art devices use a cartridge to contain the medicament. However, these prior art devices require the injector to be sterilized, usually between each use.

BRIEF DESCRIPTION OF THE PRESENT INVENTION

The present invention provides a reusable, small and easy to use, relatively low cost jet injector device adapted to be used with a disposable cartridge containing the substance to be injected. The injector, hereinafter sometimes referred to as the "gun", is spring powered in order to make it readily reusable. In order to use the jet injector of the present invention, the gun is first cocked by compressing the power spring. The gun may be cocked by pressing it against the hard surface, with relatively little force required to cock the gun. A cartridge containing a predetermined amount of the medicament to be injected is loaded onto the gun. In order to load the gun, the open end of the cartridge is inserted into cartridge engaging end of the gun and locked by rotating the cartridge a quarter turn. The engagement of the cartridge on the gun is simple and does not require substantial force. The medicament is injected by placing the closed end of the cartridge against the skin of the person to receive the medicament, and pushing a trigger button on the other end of the gun. The cartridge is removed from the gun by a quarter turn rotation of the cartridge.

The cartridge which is designed to be used with the gun of the present invention is designed to be inserted on the gun easily and removed from the gun easily. The cartridge is readily sterilizable and is easy to maintain in its sterile condition. It is not necessary that the gun be sterile in order to administer a sterile dosage to the patient.

The gun is designed to work with a variety of cartridges which may be produced in different lengths or in different internal diameters and thereby filled with different quantities of medicament to be injected. In this way cartridges containing different dosages may be applied using the same gun without the need to make adjustments to the gun. The gun of the present invention is also adapted to be adjusted by the use of different springs and/or spacers to adapt to different cartridges.

The gun of the present invention may be used to inject materials into humans, as well as animals or other substrates. Any liquid material can be loaded into the cartridge for injection.

DESCRIPTION OF THE DRAWINGS

The advantages of the present invention will be more fully understood by consideration of the following description and drawings, wherein:

FIG. 1 is a longitudinal view, taken in cross-section, of the gun of the present invention in its cocked, ready-to-fire position;

FIG. 2 is a longitudinal view, taken in cross-section, of the gun of the present invention in its fired position;

FIG. 3 is an isometric view of the cartridge of the present invention;

FIG. 4 is a front view of the gun of the present invention with a cartridge inserted but not locked;

FIG. 5 is a front view of the gun of the present invention with a cartridge inserted and locked therein; and FIG. 6 is a partial longitudinal view, taken in cross-section, of the gun of the present invention in the ready-to-fire position with a cartridge inserted therein.

DETAILED DESCRIPTION OF THE PRESENT INVENTION

Having reference to the drawings, and particularly FIGS. 1 and 2, the gun comprises barrel 10 which serves as a hand-gripping member for the gun and as a housing for piston assembly 20, spring assembly 60, trigger assembly 70 and cartridge engagement means 90. , As shown in FIGS. 1 and 2, the barrel 10 comprises cylindrical front portion 12, which is closed by front wall 13 and cylindrical rear portion 14, which is closed by back wall 15. Front portion 12 and rear portion 14 are joined by threads 16. Piston guide 18 is coaxially mounted within barrel 10.

Piston assembly 20 is preferably coaxially disposed within barrel 10, and is adapted to reciprocate longitudinally along the axis of barrel 10 within piston guide 18. Piston assembly 20 generally comprises the cartridge plunger 22, piston head 24, bearing surface 26 and trigger engaging notch 36. Preferably the piston is fabricated from a single piece of hardened steel, and more preferably from stainless steel. Those skilled in the art will understand that other materials and multi-piece constructions may be used.

Cartridge plunger 22 is adapted to extend into cartridge 100 when cartridge 100 is inserted and locked to the gun, as is shown in FIG. 6. When the gun is fired, plunger 22 is thrust longitudinally into cartridge 100 at a controlled rate, whereby a jet of the medicament packaged in the cartridge is sprayed from the cartridge at the selected velocity.

Piston head 24 is an enlarged cylindrical portion of piston assembly 20. Piston head 24 is adapted to contact the front wall of barrel 10 at the end of the firing stroke and serve to limit the forward movement of the piston at the end of the firing stroke.

Piston bearing surface 26 cooperates with piston guide 18 in barrel 10 to maintain cartridge plunger 22 in alignment with cartridge 100, and preferably to maintain piston assembly 20 in alignment with the axis of barrel 10 throughout the cocking and firing of the gun. Piston guide 18 preferably includes longitudinal vents 28 which provide a passageway for air between front portion 12 of barrel 10 and rear portion 14 of barrel 10 as the piston mechanism is cocked and/or fired. Flange 30 extends radially outward from piston guide 18 and serves to lock piston guide 18 in place with respect to barrel 10. Notch 32, located at the junction between front portion 12 and rear portion 14 of barrel 10, engages flange 30, and serves to lock piston guide 18 in a centered position within barrel 10 and thus center piston assembly 20 within barrel 10.

Trigger engaging notch 36 of piston assembly 20 is adapted to engage the trigger assembly and hold the piston assembly 20 in the ready-to-fire position thus allowing cartridge 100 to be engaged on the gun. Thereafter, the cartridge is prepared for firing.

Spring retainer 40 surrounds the outer portion of piston head 24. Spring retainer 40 includes internal shoulder 42 which bears against piston head 24. The outer periphery of spring retainer 40 defines bearing surface 44 which cooperates with the internal surface of barrel 10 and guides piston 20 in its stroke and maintains piston 20 coaxially within barrel 10 throughout the cocking and firing of the gun.

Spring retainer 40 includes 2 spring bearing surfaces 46 and 48. Long spring bearing surface 46 abuts the front surface of long spring 62. Short spring bearing surface 48 abuts the front surface of short spring 66. When the gun is in the ready-to-fire position, as is shown at FIG. 1, both springs 2 and 66 are compressed. During the cocking of the gun, as piston assembly 20 starts to move to the rear, long spring 62 is compressed between bearing surface 46 and piston guide 18. As the rearward movement of piston assembly 20 continues, short spring 66 is compressed between surface 48 and piston guide 18. The rearward movement continues until trigger engaging notch 36 reaches trigger assembly 70 and sear 82 engages notch 36. When the gun is fired by releasing sear 82 from notch 36, short spring 66 expands fully as the piston assembly 20 is thrust toward cartridge 100, thus providing piston assembly 20 with an initial high energy thrust. Thereafter, the continued expansion of long spring 62 continues to thrust piston assembly 20 toward cartridge 100. Spring retainer 40 includes guide surface 50, disposed within long spring 62, serves to maintain long spring 62 in coaxial relationship to the axis of barrel 10 while the gun is in the cocked position and the when the gun is fired.

Spring retainer 40 includes at least one longitudinal vent 52 which allows air to pass the spring retainer 40 as the spring retainer moves through the barrel when the gun is fired or cocked.

Spring assembly 60, in the embodiment shown in the drawings, is made up of long spring 62 and short spring 66. When the gun is in the ready-to-fire position, both the long spring 62 and short spring 66 are compressed between the respective shoulders 46 and 48 of spring retainer 40 and piston guide 18. When the trigger is released to fire the gun, both springs initially propel the piston assembly 20 toward the cartridge 100 and produce the instantaneous high energy jet of medicament from cartridge 100, in order to pierce the skin with the initial injection of the medicament. After a short travel, the expansion of short spring 66 is completed and the continued movement of the plunger 22 into the cartridge is driven by long spring 62. This movement continues the ejection of the jet of medicament from cartridge 100 through the aperture in the skin created by the initial high intensity burst.

Trigger assembly 70 comprises trigger button 72 and trigger cam 74 which is pivotally connected, through pin 76, to rear portion 14 of barrel 10. Trigger button 72 preferably protrudes through the back wall 15 of the rear portion 14 of barrel 10. Plunger 78 and spring 80 urge the trigger cam 74 into the engaged position, which allows sear 82 of cam 74 to engage trigger engaging notch 36 of piston 20. Spring 80, which urges cam 74 to pivot into the engaged position, also urges trigger button 72 to the rear, where button 72 is positioned to be pushed to initiate the gun firing process. Vent 73 in back wall 15 allows air to pass through the back wall 15 as the gun is cocked and/or fired.

Cartridge engaging means 90 is positioned on the front wall 13 of front portion 12 of barrel 10. The cartridge engaging means 90 comprises axial opening 92 and one or more locking shoulders 96. Opening 92 is positioned coaxially with cartridge plunger 22 and is adapted to allow cartridge plunger 22 to protrude there-through and into cartridge 100. Opening 92 is preferably sized to allow the collar 110 of cartridge 100 to fit snugly within opening 92.

As is shown in FIGS. 4 and 5 in the drawings, locking shoulders 96 define parallel walls of slot 94. As is shown in FIG. 1, slot 94 extends outwardly from front wall 13. Slot 94 is wide enough to receive cartridge collar 110 and cartridge flange 112 when cartridge 100 is inserted into the gun, as is shown in FIG. 4. Shoulder 96 includes locking slot 98, which extends perpendicular to the axis of the barrel, adjacent to front wall 13. Locking slot 98 is adapted to receive flange 112 of cartridge 100 when cartridge 100 is rotated about its axis. FIG. 5 illustrates the position of cartridge 100 after a 90 degree rotation into the locked, with flange 112 engaged to locking slot 98.

Cartridge 100 comprises a container for the medicament or other substance to be injected, which container is defined by tube 102, having a closed end 104 and a stopper 106 positioned within tube 102. Tube 102 is made from a sterilizable material such as polypropylene, polyethylene or nylon. The interior of tube 102 is a smooth cylindrical shape. The exterior surface of tube 102 may be knurled in order to enhance the user's gripping ability to rotate the cartridge 90 degrees to lock or unlock the cartridge to the gun.

Stopper 106 is preferably cylindrical in shape. Stopper 106 may be fabricated from neoprene or other inert and non-reactive materials. Stopper 106 is adapted to movably seal tube 102, that is, stopper 106 is moved toward the closed end 104 of tube 102 when the gun is fired.

Orifice 108 is drilled in closed end, 104 of tube 102. The diameter and length of orifice 108 is selected to control the shape and velocity of the jet of medicament emitted by the cartridge when the gun is fired. Generally it has been found that a cartridge having an orifice of about 0.005 inches in diameter in a wall (closed end 104) which is at least 5 times as thick, i.e., 0.0025 inches, and preferably 10 times as thick, i.e., 0.005 inches, is useful. The spring assembly is preferably sized to deliver about 800 psi pressure in the cartridge at the start of the stroke. Such a spring assembly requires a total force of about 22 pounds to cock the gun. It has been found that laser drilling of a 0.005 inch orifice in a polypropylene cartridge, when used with such a spring assembly, produces a jet of appropriate dimensions within acceptable tolerances.

Collar 110 is positioned on the open end of cartridge 100. Collar 110 is adapted to fit into opening 92 of the cartridge engaging means 90 of the gun. Interrupted flange 112, affixed to the exterior of the cartridge adjacent to collar 110, is adapted to fit into slot 94 between shoulders 96 when cartridge collar 110 is inserted into opening 92. Cartridge 100 is locked to the gun by inserting collar 110 into opening 92, as is shown in FIG. 4, and rotating the cartridge 90 degrees to lock interrupted flange 112 into lateral slot 98, as is shown in FIG. 5. When interrupted flange 112 is locked into lateral slot 98, cartridge 100 is locked to the gun and held in that position as the gun is fired and cartridge plunger 22 moves stopper 106 toward the closed end 104 of tube 102. Flange extensions 114 are preferably positioned on the outermost portion of flange 112 to limit the rotation of the cartridge 100 when it is rotated into the locked position in the gun. Alternatively, lug 116, positioned on the end of flange 112, may be used in order to prevent the cartridge from rotating more than about 90 degrees and sticking in the gun after use. A combination of flange extensions 114 and lugs 116 may be used to prevent the rotation of the cartridge beyond its locking position.

As is shown in FIG. 3, preferably cap 120 is fitted over the closed end 104 of cartridge 100 in order to maintain orifice 108 and closed end 104 sterile. It is also preferred to protect collar 110 from dust and dirt with cap 122. Those skilled in the art will understand that other sanitary seals for the ends of cartridge 100, such as tape, may be used in lieu of caps 120 and 122.

In order to use the jet injector of the present invention, the gun is first cocked. This may be done by placing the gun against a hard surface, such as a table, and pressing down on the gun. This forces piston assembly 20 to move toward the rear of the gun by pressure applied through plunger 22. A gun having a spring assembly designed to deliver 800 psi of pressure requires about 22 pounds of force to cock the gun. As is shown in FIG. 1, when plunger 22 is nearly within the gun, i.e., within shoulders 96, trigger cam 74, being urged by spring 80, causes sear 82 to engage trigger engaging notch 36 on piston assembly 20. At the same time, trigger button 72 is thrust backwardly through back wall 15.

Cartridge 100 is affixed to the gun simply by removing cap 122 and placing collar 110 of cartridge 100 into opening 92 of the gun. Interrupted flange 112 must be aligned with shoulders 96 to allow the interrupted flange 112 to pass shoulders 96 and into the slot 94, as is shown in FIG. 4. After the cartridge has been firmly pushed down on the gun, it is rotated 90 degrees, as is shown in FIG. 5, where it is locked to the gun. After removal of cap 120, the gun is fired by placing closed end 104 of cartridge 100 against the skin, as is shown in FIG. 2, and pressing trigger button 72. Thereafter, the spring assembly 60 drives piston assembly 20 forward, and cartridge plunger 22 causes stopper 106 to move from its initial position at the open end of cartridge 100, as shown in FIG. 6, to the closed end 104 of tube 102, as shown in FIG. 2.

After being used, cartridge 100 is removed from the gun simply by rotating 90 degrees to align flange 112 with slot 94 between shoulders 96, to the position shown in FIG. 4. Preferably, the length of cartridge 100 is slightly shorter than the length of the stroke of piston assembly 20, whereby the movement of the plug in the cartridge is completed before piston head 24 contacts the front wall 13 of the barrel 10, so that when the spent cartrige is rotated to the position shown in FIG. 4, the spring assembly thrusts the used cartridge off the gun.

The device of the present invention may be used without the need to sterilize the gun. There is no need to open the gun or make adjustments to the gun in order to fire the cartridge. It is necessary only to engage the cartridge to remove the cap 120 over the closed end which protects the orifice and then fire the gun. This enables the gun to be used under non-sterile conditions, such as in combat circumstances or in veterinary applications in the barnyard without the need to use bulky, cumbersome, sterile equipment.

The two spring assembly 60 shown in the drawings can be replaced by a single compound spring, i.e., a single spring, having a linear or differential compression requirement.

Those skilled in the art will be aware that the cartridge and the cartridge engaging means may be modified in a variety of ways. For example, a single shoulder 96 may be used with a flange with an interruption large enough to allow the cartridge to be inserted onto the gun, with collar 110 being placed in opening 92, whereby rotation of the cartridge will lock the flange within slot 94 within shoulders 96. It is preferred, however, to use a plurality of shoulders with associated locking slots, as is shown in the drawings. The present invention contemplates the use of more than shoulders, although it is preferred that they be symmetrically disposed about opening 92 in order to maintain cartridge 100 in axial alignment with the barrel 10 of the gun. The amount of rotation necessary to lock the cartridge to the gun will be affected by the number of shoulders employed. The main function of collar 110 is to hold the cartridge in proper alignment on the gun. Accordingly, the cartridge extension illustrated as collar 110 may be modified to employ a variety of non-cylindrical configurations and/or fingers to carry out the alignment function.

Spacer 130, shown in FIG. 6 within the front end of barrel 10, can be used to to limit the stroke of piston assembly 20 and thus adapt the gun for use with shorter cartridges.

The forms of invention herein shown and described are to be considered only as illustrative. It will be apparent to those skilled in the art that numerous modifications may be made therein without departure from the spirit of the invention or the scope of the appended claims.

I claim:

1. A hypodermic jet injector comprising a gun and a medicament containing cartridge; said gun comprising:
    an elongated hollow body having an opening in one end;
    piston means positioned in said elongated body to move axially and longitudinally within said elongated body, spring means urging one end of said piston means toward said opening, trigger means adapted to releasably hold said piston means away from said opening in opposition to the urging of said spring means, a plunger affixed to the one end of said piston means and extending through said opening in said one end of said elongated body;
    cartridge engaging means affixed to said one end of said elongated body, said cartridge engaging means comprising a shoulder and a slot, said shoulder connected to the exterior of said elongated body adjacent to said opening in said one end of said elongated body, said slot positioned between said shoulder and said body, transverse to the axis of said elongated body;
    said cartridge comprising:
        an elongated tube having a closed end and an open end, an orifice positioned in said closed end, a plug slidably positioned in the open end of said tube and a medicament in the space defined by said tube and said plug;
        an interrupted flange affixed to said tube adjacent to said open end, said flange extending transverse to the axis of said tube;
        a collar extending longitudinally from said tube and beyond said interrupted flange, at said open end, of said tube;
        said cartridge removably locked onto said gun by inserting said collar into the opening in said one end of the elongated body of said gun with the interruption in said flange passing over said shoulder, said collar surrounding said plunger, and rotating said cartridge, whereby said interrupted flange engages the slot in said shoulder and thereby locks said cartridge to said gun to maintain said cartridge in said locked position when said trigger means releases said piston means and said spring means urges said piston means toward said opening.

2. A hypodermic jet injector as described in claim 1, wherein said elongated body is generally cylindrical.

3. A hypodermic jet injector as described in claim 1, wherein said spring means comprises a first spring means adapted to urge said piston means toward said opening throughout the entire movement of said piston means and a second spring means adapted to urge said piston means toward said opening throughout only part of the movement of said piston means.

4. A hypodermic jet injector as described in claim 1, wherein said cartridge engaging means further comprises at least one additional shoulder connected to the exterior of said elongated body adjacent to said opening in said one end of said elongated body, a slot positioned between said additional shoulder and said body, transverse to the axis of said elongated body; and said interrupted flange of said cartridge having at least two interruptions for registration with said shoulders.

5. A hypodermic jet injector as described in claim 1, wherein said longitudinally extending collar is cylindrical.

6. A hypodermic jet injector as described in claim 1, wherein said cartridge is shorter than the length of the movement of said piston means, whereby said spring means urging said piston means toward said opening also tends to urge a spent cartridge away from said gun when said cartridge is rotated to disengage said interrupted flange from said slot in said shoulder.

* * * * *